United States Patent
Choi et al.

(10) Patent No.: US 8,666,503 B2
(45) Date of Patent: Mar. 4, 2014

(54) PARAMETER ADJUSTMENT DEVICE AND METHOD THEREOF

(75) Inventors: Charles Tak Ming Choi, Hsinchu (TW); Yi-Hsuan Lee, Taichung (TW)

(73) Assignee: National Chiao Tung University, Hsinchu (TW)

(*) Notice: Subject to any disclaimer, the term of this patent is extended or adjusted under 35 U.S.C. 154(b) by 657 days.

(21) Appl. No.: 12/627,192

(22) Filed: Nov. 30, 2009

(65) Prior Publication Data

US 2010/0292751 A1    Nov. 18, 2010

(30) Foreign Application Priority Data

May 12, 2009   (TW) .............................. 98115755 A

(51) Int. Cl.
    *A61N 1/36*     (2006.01)
(52) U.S. Cl.
    USPC ............................................................ 607/57
(58) Field of Classification Search
    USPC .................. 607/30, 59, 45, 46, 55–57, 62
    See application file for complete search history.

(56) References Cited

U.S. PATENT DOCUMENTS 7,043,303 B1 *  5/2006  Overstreet ...................... 607/57

* cited by examiner

*Primary Examiner* — Christopher D Koharski
*Assistant Examiner* — Michael D Abreu
(74) *Attorney, Agent, or Firm* — WPAT, P.C.; Anthony King

(57) ABSTRACT

A parameter adjustment device and method thereof for a stimulator is disclosed. The parameter adjustment device comprises a generation unit, a user interface and a process unit. The generation unit generates a test MAP based on a current MAP. The user interface displays the current MAP and the test MAP for choosing one of them as the preferred MAP, and displays a major and a minor for choosing again, the major and the minor is defined as a significant difference and a little difference between the test MAP and the current MAP respectively. The process unit computes the acceptance probability of the preferred MAP based on a major or minor probability correspondence relationship and determines a next MAP by comparing the acceptance probability with the test probability. When one of the termination conditions is satisfied in an iterative operation, the next MAP is outputted as the best MAP.

7 Claims, 4 Drawing Sheets

PARAMETER ADJUSTMENT DEVICE AND METHOD THEREOF

BACKGROUND OF THE INVENTION

1. Field of the Invention

The present invention relates to a parameter adjustment device and a method thereof; in particular, the present invention relates to a parameter adjustment device and a method thereof for adjusting stimulating parameters in a stimulator by means of an iterative operation based on the simulated annealing method.

2. Description of Related Art

A stimulator is a type of device able to generate stimulation signals, which, when applied in medical usages, allows to stimulate a user's nerves or muscular organization, thereby achieving the purposes of diagnoses, rehabilitations or therapies. When the stimulator is applied in the medical field, it can be used to improve or treat neural system diseases like neural function imbalance or impairment. For example, Cochlear Implant (CI) can be used to improve severe to profound hearing loss condition. Deep Brain Stimulator (DBS) can be used to treat Parkinson's Disease. Vagus Nerve Stimulation (VNS) can treat epilepsy. Spinal Cord Stimulator (SCS) can be used to treat chronic disease pains or to improve spinal injury conditions. Sacral Nerve Stimulation (SNS) can treat urinary incontinence.

Due to different causes or reasons in every user's various symptoms and conditions, most of the stimulators are equipped with the function of parameter adjustment, in order to adjust the control parameters of the stimulator, thereby allowing the stimulation signal generated by the stimulator to be applicable for different types of users. The control parameters refer to parameters such as voltage amplitude, current amplitude, pulse width, pulse frequency and duration etc., which enable generation of stimulation signal by the stimulator. However, parameter adjustment may need to consume a lot of time and manual efforts, and usually requires multiple times of clinical tests and error fixings, amending the values for the set of the control parameters one by one, thereby generating the best values for the set of the control parameters. The best values for the set of the control parameters allow the stimulator to suitably provide the optimal stimulation outcome and the least side effect. But, the control parameters are mutually interrelated in most cases, e.g. the input voltage amplitude affects the output pulse width, thus in addition to the inconsistencies between the user's bio-physical features and feedback information, the generation of the best control parameter would become even more challenging.

SUMMARY OF THE INVENTION

In view of the aforementioned problems found in prior art, one objective of the present invention is to provide a parameter adjustment device and a method thereof as the implementations and bases for improvements on the above-said drawbacks.

According to another objective of the present invention, herein is proposed a parameter adjustment device applicable for a stimulator, comprising: a generation unit, a user interface and a process unit. The generation unit generates a test MAP based on a current MAP. A MAP comprises of a set of stimulating parameters. The stimulating parameters are voltage amplitude, current amplitude, pulse width, pulse frequency and duration etc. When one value of the set parameters is changed, a different set of parameters may be mapped. In the first iteration, the current MAP is an initial MAP generated by the generation unit, and the test MAP and current MAP are the values for the set of the parameters, and the generation unit generates the test MAP by changing the values for the set of parameters based on the current MAP. The user interface displays the current MAP and the test MAP for choosing the current MAP or the test MAP as a preferred MAP, and displays a major and a minor for the user to choose the major or minor, the major and the minor is defined as a significant difference and a little difference between the test MAP and the current MAP respectively. The user chooses the current MAP and test MAP respectively for sensing the stimulating signals, and the preferred MAP is the preferred signal for stimulating. The process unit computes an acceptance probability of the preferred MAP based on a major probability correspondence relationship or a minor probability correspondence relationship. Then, the process unit determines a next MAP by comparing the acceptance probability and the test acceptance probability, and. Herein, when one of the termination conditions is satisfied in an iterative operation, the next MAP is outputted as the best MAP. Herein, when none of the termination conditions is satisfied, the next MAP is subject to the iterative operation through the generation unit, the user interface and the process unit, until one of the termination conditions is satisfied. In other word, if one of the termination conditions in iteration i, the next MAP will be outputted. If not, the next MAP will become the current MAP in iteration i+1.

Herein, when the preferred MAP is the current MAP and the process unit determines to accept the preferred MAP, then the current MAP is defined as the next MAP.

Herein, when the preferred MAP is the test MAP and the process unit determines to accept the preferred MAP, then the test MAP is defined as the next MAP.

Herein, when the preferred MAP is the current MAP and the process unit determines not to accept the preferred MAP, then the test MAP is defined as the next MAP.

Herein, when the preferred MAP is the test MAP and the process unit determines not to accept the preferred MAP, then the current MAP is defined as the next MAP.

Herein, when the process unit compares the acceptance probability to be greater than the test acceptance probability, then the preferred MAP is accepted.

Herein, when the process unit compares the acceptance probability to be smaller than or equal to the test acceptance probability, then the preferred MAP is not accepted.

Herein, the termination conditions comprise receiving a termination command, terminating an iterative operation at a prescribed number or determinating the preferred MAP as the minor in accumulated times.

Herein, the stimulator may be a Cochlear Implant (CI), a Deep Brain Stimulator (DBS) or a Spinal Cord Stimulator (SCS).

According to yet another objective of the present invention, herein is proposed a parameter adjustment method applicable for a stimulator, comprising the following steps: STEP A, generating a test MAP based on a current MAP by means of a generation unit; STEP B, choosing the current MAP or the test MAP as a preferred MAP through a user interface; STEP C, choosing a major or a minor through the user interface, the major and the minor is defined as a significant difference and a little difference between the current MAP and the test MAP respectively; STEP D, computing the acceptance probability of the preferred MAP based on the major probability correspondence relationship or the minor probability correspondence relationship by using a process unit; STEP E, determining a next MAP by comparing the acceptance probability with the test acceptance probability through the process unit;

and; STEP F, outputting the next MAP as a best MAP through the process unit when one of the termination conditions is satisfied in a iterative operation. Herein, when none of the termination condition is satisfied, the next MAP is subject to the iterative operation through STEP A to STEP E, until one of the termination conditions is satisfied.

Herein, when the preferred MAP is the current MAP and the preferred MAP is accepted, then the current MAP is defined as the next MAP.

Herein, when the preferred MAP is the test MAP and the preferred MAP is accepted, then the test MAP is defined as the next MAP.

Herein, when the preferred MAP is the current MAP and the process unit does not accept the preferred MAP then the test MAP is defined as the next MAP.

Herein, when the preferred MAP is the test MAP and the process unit does not accept the preferred MAP, then the current MAP is defined as the next MAP.

Herein, when the acceptance probability is greater than the test acceptance probability, then the preferred MAP is accepted.

Herein, when the acceptance probability is smaller than or equal to the test acceptance probability, then the preferred MAP is not accepted.

Herein, the termination conditions comprise receiving a termination command, terminating an operation at a prescribed number of iterative operations or at the accumulated times of determination as a minor.

Herein, the stimulator may be a Cochlear Implant (CI), a Deep Brain Stimulator (DBS) or a Spinal Cord Stimulator (SCS).

In summary of the descriptions as above, the parameter adjustment device and the method thereof according to the present invention provides one or more following advantages:

(1) The parameter adjustment device and the method thereof according to the present invention allows to adjust the control parameters of the stimulator in accordance with the user's feedback information;

(2) The parameter adjustment device and the method thereof according to the present invention is based on the simulated annealing method, thereby improving the efficiency with regards to the generation for the control parameters of the stimulator;

(3) The parameter adjustment device and the method thereof according to the present invention enables customized operations and adjustments on the control parameters of the stimulator by the user.

DETAILED DESCRIPTION OF THE PREFERRED EMBODIMENTS

Figure 1:
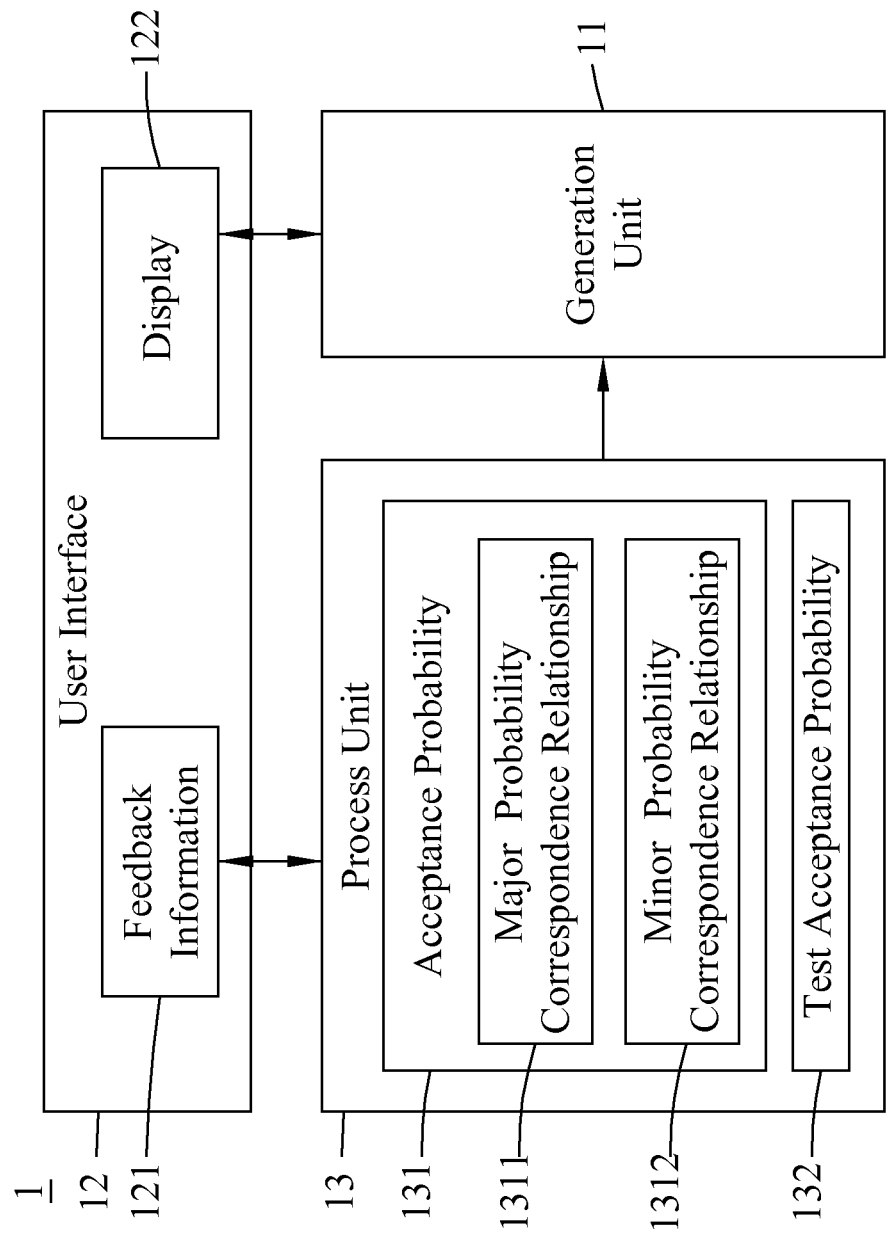
FIG. 1 is a diagram for an embodiment of the parameter adjustment device according to the present invention.

Reference can be first made to FIG. 1, wherein a diagram for an embodiment of the parameter adjustment device according to the present invention is shown. As illustrated in the Figure, the parameter adjustment device 1 comprises a generation unit 11, a user interface 12 and a process unit 13. When the parameter adjustment device 1 is applied to a stimulator, the generation unit 11 of the parameter adjustment device 1 generates a test MAP based on a current MAP. A MAP comprises of a set of stimulating parameters. The stimulating parameters may be voltage amplitude, current amplitude, pulse width, pulse frequency and duration etc. When one value of the set parameters is changed, a different set of parameters may be mapped. In the first iteration, the current MAP is an initial MAP generated by the generation unit, and the test MAP and current MAP are the values for the set of the parameters, and the generation unit generates the test MAP by changing the values for the set of parameters based on the current MAP. The user interface 12 displays the current MAP and a test MAP through the user interface 12, then the user may choose the current MAP and the test MAP to sense the difference demonstrated by the stimulation signal. For example, when the stimulation signal is an audible stimulation signal, the user can sense the clarity or comfort and use this as the basis of a preferred MAP. When the user is certain about a preferred MAP, the user interface 12 may display the property options for choosing the preferred MAP as a major or a minor, thereby allowing the user to choose once again. Then the user may specify a significant difference or a little difference as the major or the minor respectively. Taking the audible stimulation signal for example, the user can choose the stimulation signal to be "Significantly Improved", "Slightly Improved" or "No Improvement" then use this as the basis for choosing the property options of the major or the minor. In case the user senses that the stimulation signal indicates "Significantly Improved", the preferred MAP is selected as the major; while the user feels the stimulation signal corresponds to "Slightly Improved" or "No Improvement", the preferred MAP is selected as the minor. After determination of being a major or a minor, the user interface generates the feedback information 121.

The process unit 13 receives the feedback information 121 and calculates the acceptance probability 131 of the preferred MAP based on a major probability correspondence relationship 1311 or a minor probability correspondence relationship 1312. Then, the process unit 13 randomly generates a test acceptance probability 132 for enabling comparison of the acceptance probability 131 and the test acceptance probability 132; next, the process unit 13 determines a next MAP based on the comparison result.

The user can perform different settings based on actual usages so as accept preferred MAP or not, when the process unit 13 compares the acceptance probability 131 to be smaller than or equal to the test acceptance probability 132, then the preferred MAP is not accepted, and when the process unit 13 compares the acceptance probability 131 to be greater than the test acceptance probability 132, the preferred MAP is accepted. Or else, in another configuration, when the process unit 13 compares the acceptance probability 131 to be smaller than or equal to the test acceptance probability 132, then the preferred MAP is accepted, and when the process unit 13 compares the acceptance probability 131 to be greater than the test acceptance probability 132, the preferred MAP is not accepted. Herein the purpose of the test acceptance probability 132 is to prevent a condition that the preferred MAP falls within local optimum.

The process unit 13 may acquire the next MAP based on the comparison result. In case when one of the termination conditions is satisfied in the iterative operation, the process unit 13 outputs the next MAP as the best MAP. Otherwise, in case none of the termination conditions is satisfied, the next MAP is subject to the iterative operation through the generation unit 11, the user interface 12 and the process unit 13, until the termination condition is satisfied. In other word, if one of the termination conditions in iteration i, the next MAP will be outputted. If not, the next MAP will become the current MAP in iteration i+1.

The above-mentioned termination conditions comprise the following three cases; Case 1, when the iterative operation reaches a prescribed number, the process unit 13 terminates the iterative operation, and outputs the next MAP through the process unit 13 to the user interface 12, thereby allowing the user to choose the present stimulation parameter; Case 2, when the number of determining the preferred MAP as the minor by the user has reached a prescribed number, the iterative operation is terminated. For example, in the condition that the user determinates the stimulation signal is slightly improved or no improvement at a prescribed number, the process unit receives user's feedback, then the process unit 13 terminates the iterative operation; Case 3, when the user inputs a termination command over the user interface 12, the user interface 12 generates the feedback information 121 and the process unit 13 receives such feedback information 121, then the iterative operation is terminated through the process unit 13.

In a preferred embodiment, when the user chooses the current MAP as the preferred MAP by means of the user interface 12 and determines the current MAP as the major, the process unit 13 computes the acceptance probability 131 of the current MAP based on the major probability correspondence relationship 1311. Then the process unit 13 compares the acceptance probability of the current MAP and the test acceptance probability, and determines whether to accept the current MAP as the next MAP based on the comparison result. When the comparison result is that the current MAP is accepted as the next MAP, the process unit 13 selects the current MAP as the next MAP. On the other hand, when the comparison result is that the current MAP is not accepted as the next MAP, the process unit 13 selects the test MAP as the next MAP. When none of the termination conditions is satisfied, the next MAP is subject to the iterative operation through the generation unit 11, the user interface 12 and the process unit 13, until one of the termination conditions is satisfied. In case one of the termination conditions is satisfied in the iterative operation, the process unit 13 outputs the next MAP.

When the user chooses the test MAP as the preferred MAP over the user interface 12 and determines the test MAP as the minor, the process unit 13 computes the acceptance probability 131 of the test MAP based on the minor probability correspondence relationship 1312. Then the process unit 13 compares the acceptance probability 131 of the test MAP with the test acceptance probability 132, and determines whether to accept the test MAP as the next MAP based on the comparison result. When the comparison result is that the test MAP is accepted as the next MAP, the process unit 13 selects the test MAP as the next MAP. On the other hand, when the comparison result is that the test MAP is not accepted as the next MAP, the process unit 13 selects the current MAP as the next MAP. When none of the termination conditions is satisfied, the next MAP is subject to the iterative operation through the generation unit 11, the user interface 12 and the process unit 13, until one of the termination conditions is satisfied. In case one of the termination conditions is satisfied, the process unit 13 outputs the next MAP.

In accordance with the difference in the number of iterative operations, the preferred MAP is not limited to the aforementioned current MAP and the test MAP. Besides, the parameter adjustment device 1 according to the present invention can be applied to a stimulator, where the simulator may be a Cochlear Implant (CI), a Deep Brain Stimulator (DBS) or a Spinal Cord Stimulator (SCS).

Figure 2:
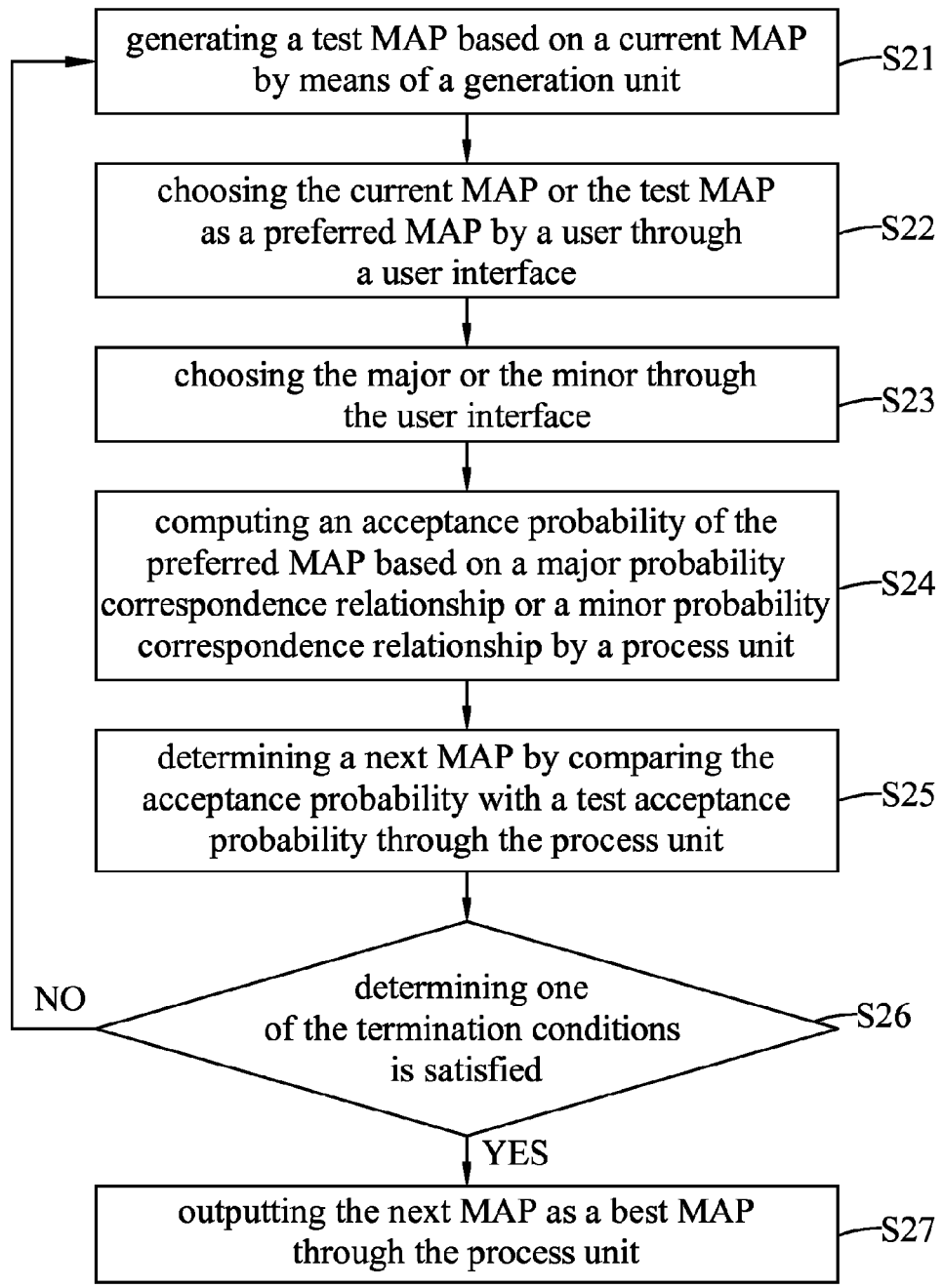
FIG. 2 is a flowchart for an embodiment of the parameter adjustment method according to the present invention.

Refer now to FIG. 2, wherein a flowchart for an embodiment of the parameter adjustment method according to the present invention is shown. As illustrated in the Figure, the parameter adjustment method applicable for a stimulator comprises the following steps: STEP S21, generating a test MAP based on a current MAP by means of a generation unit; STEP S22, choosing the current MAP or the test MAP as a preferred MAP by a user through a user interface; STEP S23, choosing a major or a minor through the user interface, the major and the minor are defined as a significant difference and a little difference between the current MAP and the test MAP respectively; STEP S24, computing the acceptance probability of the preferred MAP based on the major probability correspondence relationship or the minor probability correspondence relationship by a process unit; STEP S25, determining a next MAP by comparing the acceptance probability with a test acceptance probability through the process unit; STEP S26, determining one of the termination conditions is satisfied in the iterative operation; if yes, then performing STEP S27; otherwise, the next MAP is subject to the iterative operation in STEP S21 to STEP S26 until one of the termination conditions is satisfied. Herein the termination conditions comprise receiving a termination command, terminating the iterative operation at a prescribed number or determinating the preferred MAP as the minor in the accumulated times and satisfying the aforementioned condition; STEP S27, outputting the next MAP as the best MAP through the process unit.

When the user chooses the current MAP and the process unit accepts the current MAP, the process unit outputs the current MAP and the current MAP is defined as the next MAP for the iterative operation, until one of the termination conditions is satisfied. On the other hand, when the user chooses the test MAP and the process unit accepts the test MAP, the process unit outputs the test MAP or the test MAP is defined as the next MAP for the iterative operation, until one of the termination conditions is satisfied.

Additionally, when the user chooses the current MAP and the process unit does not accept the current MAP, the process unit outputs the test MAP and the test MAP is defined as the next MAP for the iterative operation, until one of the termination conditions is satisfied. Whereas, when the user chooses the test MAP and the process unit does not accept the test MAP, the process unit outputs the current MAP and the current MAP is defined as the next MAP for the iterative operation, until one of the termination conditions is satisfied.

Upon comparing the acceptance probability and the test acceptance probability, it is possible to determine the next MAP based on the comparison result. The user can perform different settings based on actual usages so as to accept preferred MAP or not. Taking the present embodiment for example, when the acceptance probability is compared to be smaller than or equal to the test acceptance probability, the preferred MAP is not accepted; and when the acceptance probability is compared to be greater than the test acceptance probability, the preferred MAP is accepted. Or else, in another configuration, when the acceptance probability is compared to be smaller than or equal to the test acceptance probability, then the preferred MAP is accepted, and when the acceptance probability is compared to be greater than the test acceptance probability, the preferred MAP is not accepted.

The parameter adjustment method according to the present invention can be applied to a stimulator, in which the simulator may be a Cochlear Implant (CI), a Deep Brain Stimulator (DBS) or a Spinal Cord Stimulator (SCS).

Figure 3:
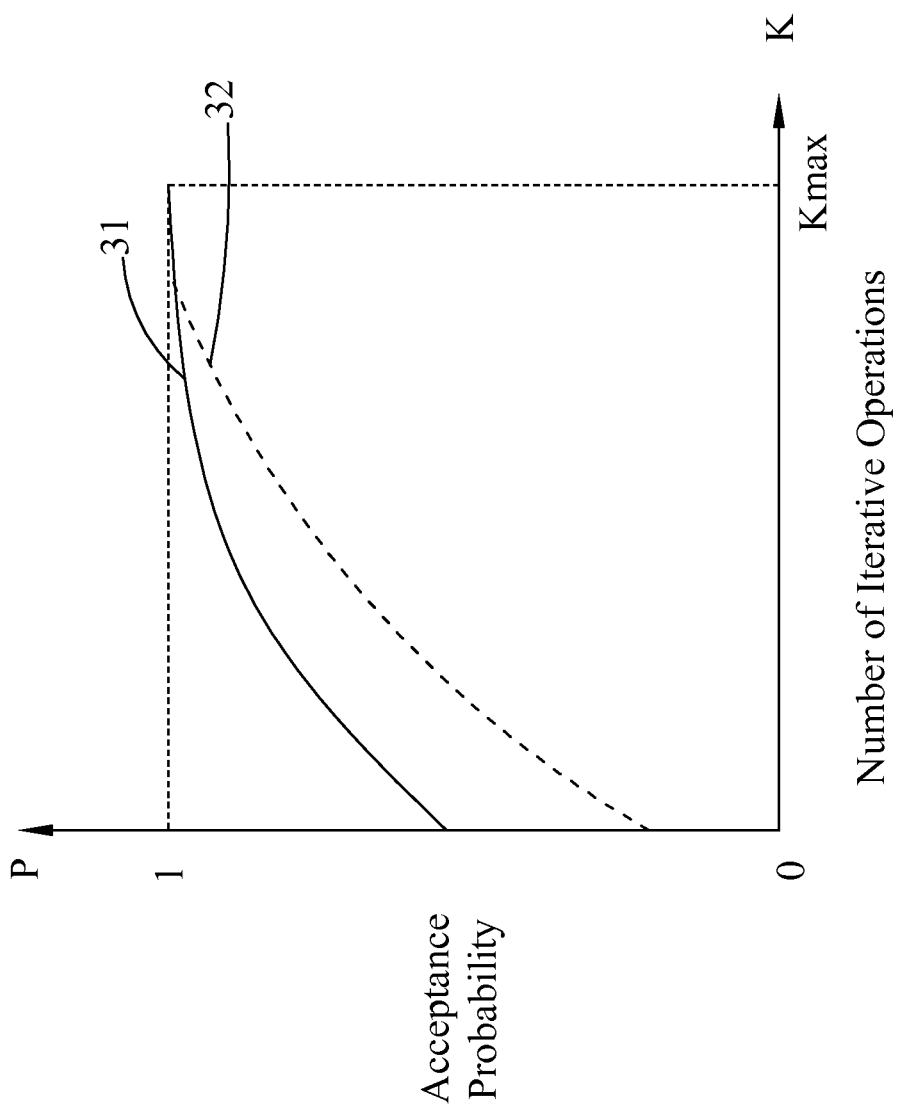
FIG. 3 is a diagram for the acceptance probability correspondence relationship of the parameter adjustment device and the method thereof according to the present invention.

Refer next to FIG. 3, wherein a diagram for the acceptance probability correspondence relationship of the parameter adjustment device and method thereof according to the present invention is shown. The Figure illustrates the functional relationships between the number of iterative operations versus the acceptance probability. By using the user feedback information generated through the user interface, when the user determines the preferred MAP as the major, the process unit selects the acceptance probability function curve 31 of the major, thus allowed to calculate the acceptance probability of the major. When the user determines the preferred MAP as the minor, the process unit selects the acceptance probability function curve 32 of the minor, thus allowed to calculate the acceptance probability of the minor. According to different numbers of iterative operations, it is possible to acquire the various acceptance probabilities for different numbers of operations.

Figure 4:
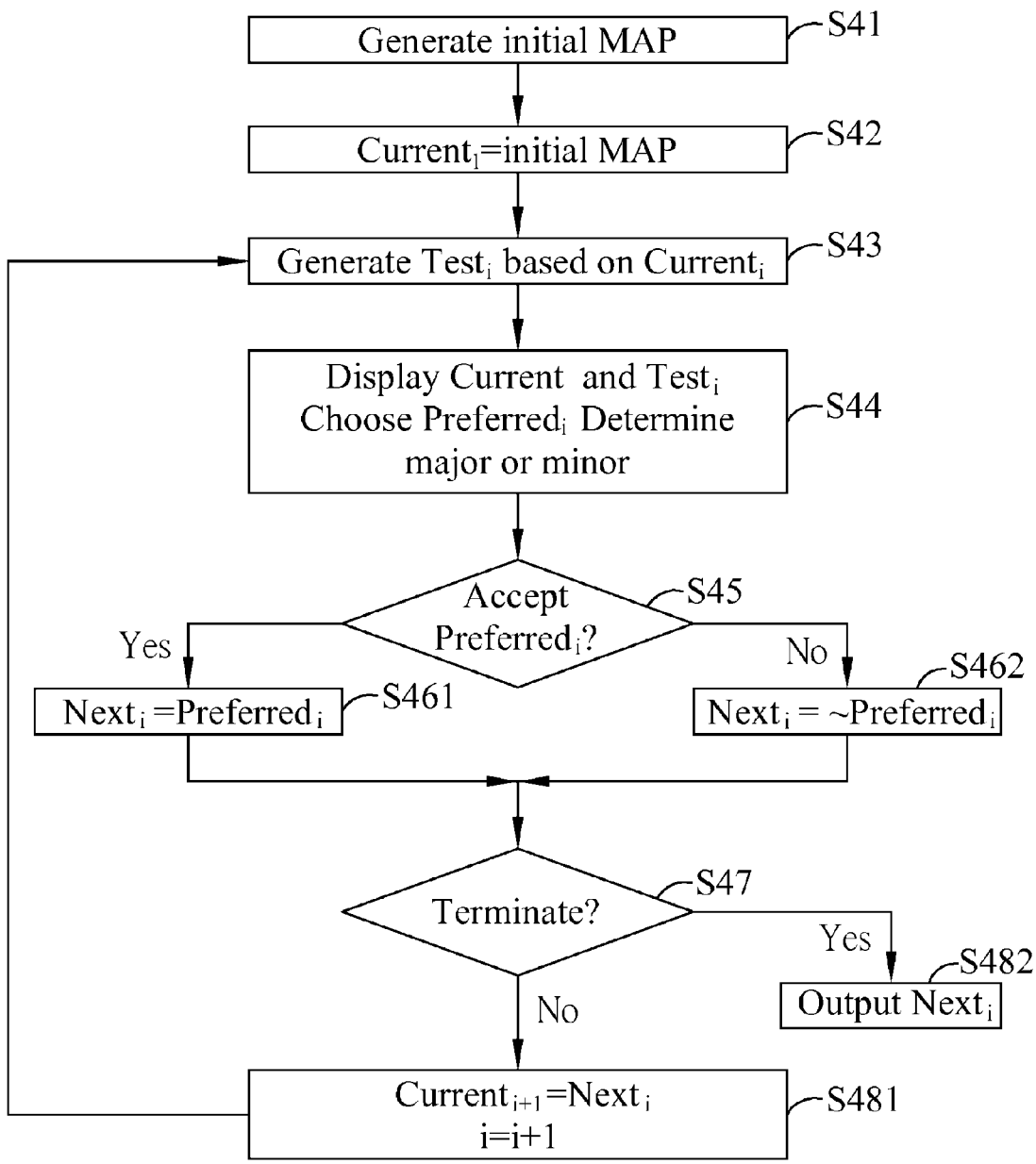
FIG. 4 is a flowchart for the MAP in the parameter adjustment device according to the present invention.

Please refer to FIG. 4, wherein a flowchart for the MAP in the parameter adjustment device according to the present invention is shown. As illustrated in the Figure, STEP S41, the generation unit generates an initial MAP. STEP S42, the generation unit uses the initial MAP as the current MAP. STEP S43, the generation unit generates a test MAP based on the current MAP. STEP S44, the user interface displays the current MAP and the test MAP for choosing the current MAP or the test MAP as the preferred MAP, and then the user determinates the preferred MAP is the major or the minor through the user interface. STEP S45, the process unit computes the acceptance probability of the preferred MAP for determinating to accept the preferred MAP or not. If the process unit accepts the preferred MAP, then performing STEP S461, the preferred MAP becomes the next MAP; otherwise, the process unit chooses ~preferred MAP as the next MAP. STEP S47, the process unit determinates one of the termination conditions is satisfied in iterative operation; if yes, then performing STEP S482, the next MAP is outputted; if no, then performing STEP S481, the next MAP will become the current MAP, and the next MAP is subject to the iterative operation in STEP S43 to STEP S47 until one of the termination conditions is satisfied.

The aforementioned descriptions are exemplary, rather than being restrictive. All effectively equivalent changes or modifications made thereto without departing from the spirit and scope of the present invention are deemed to be encompassed by the claims set forth hereunder.

What is claimed is:

1. A parameter adjustment method to acquire a best MAP, the method being applicable for a stimulator, and consisting the following steps of using an iterative operation:

predetermining a probability correspondence relationship of a major and a probability correspondence relationship of a minor by a process unit and storing the probability correspondence relationship of the major and the probability correspondence relationship of the minor in the process unit;

predetermining a current MAP of a first iteration being part of the iterative operation;

generating a test MAP by adjusting parameters of the current MAP by a generation unit;

choosing the current MAP or the test MAP as a preferred MAP by a user through a user interface according to demonstrated stimulation signals of the current MAP and the test MAP generated by the stimulator;

determining that the preferred MAP is the major or the minor through the user interface according to an improvement between the demonstrated stimulation signals of the current MAP and the test MAP generated by the stimulator;

determining an acceptance probability of the preferred MAP based on the probability correspondence relationship of the major or the probability correspondence relationship of the minor by the process unit;

randomly generating a test acceptance probability by the process unit;

determining a next MAP by comparing the acceptance probability with the test acceptance probability through the process unit; and outputting the next MAP as the best MAP through the process unit when one of termination conditions is met during the iterative operation; wherein when none of the termination conditions is met, the next MAP is subject to the iterative operation through the aforementioned steps, until one of the termination conditions is satisfied, the next MAP of a $i^{th}$ iteration is set as the current MAP of a $i+1^{th}$ iteration.

2. The parameter adjustment method according to claim 1, wherein when the preferred MAP is the current MAP and the preferred MAP fails to be the next MAP, the process unit uses the test MAP as the next MAP.

3. The parameter adjustment method according to claim 1, wherein when the preferred MAP is the test MAP and the preferred MAP fails to be the next MAP, the process unit uses the current MAP as the next MAP.

4. The parameter adjustment method according to claim 1, wherein when the acceptance probability is greater than the test acceptance probability, the process unit uses the preferred MAP as the next MAP.

5. The parameter adjustment method according to claim 1, wherein when the acceptance probability is smaller than or equal to the test acceptance probability, the process unit does not use the preferred MAP as the next MAP.

6. The parameter adjustment method according to claim 1, wherein the termination conditions comprise receiving a termination command, terminating an operation at a prescribed number of iterative operations or determinating the preferred MAP as the minor in accumulated times.

7. The parameter adjustment method according to claim 1, wherein, the stimulator may be a Cochlear Implant (CI), a Deep Brain Stimulator (DBS) or a Spinal Cord Stimulator (SCS).

* * * * *